(12) United States Patent
Rabe et al.

(10) Patent No.: US 8,231,292 B2
(45) Date of Patent: Jul. 31, 2012

(54) APPARATUS AND METHODS FOR MODIFYING KERATINOUS SURFACES

(75) Inventors: Thomas Elliot Rabe, Baltimore, MD (US); David Edward Wilson, Reisterstown, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 354 days.

(21) Appl. No.: 12/688,751

(22) Filed: Jan. 15, 2010

(65) Prior Publication Data

US 2010/0224210 A1    Sep. 9, 2010

Related U.S. Application Data

(60) Provisional application No. 61/145,344, filed on Jan. 16, 2009, provisional application No. 61/145,350, filed on Jan. 16, 2009, provisional application No. 61/145,358, filed on Jan. 16, 2009, provisional application No. 61/145,365, filed on Jan. 16, 2009, provisional application No. 61/145,371, filed on Jan. 16, 2009, provisional application No. 61/145,378, filed on Jan. 16, 2009.

(51) Int. Cl.
*A46B 11/00* (2006.01)

(52) U.S. Cl. ........................................ 401/19
(58) Field of Classification Search ............ 401/208, 401/209, 219, 220
See application file for complete search history.

(56) References Cited

U.S. PATENT DOCUMENTS

| | | |
|---|---|---|
| 2,995,521 A | 8/1961 | Bluard |
| 3,541,581 A | 11/1970 | Monson |
| 4,405,489 A | 9/1983 | Sisbarro |
| 4,528,111 A | 7/1985 | Su |
| 4,651,503 A | 3/1987 | Anderson |
| 5,133,280 A * | 7/1992 | Kubo ............................ 118/259 |
| 5,143,722 A | 9/1992 | Hollenberg |
| 5,160,315 A | 11/1992 | Heinecke et al. |
| 5,248,495 A | 9/1993 | Patterson |
| 5,308,643 A | 5/1994 | Osipow |
| 5,326,556 A | 7/1994 | Barnet |
| 5,495,338 A | 2/1996 | Gouriou et al. |
| 5,497,699 A | 3/1996 | Mather |
| 5,500,211 A | 3/1996 | George |
| 5,614,310 A | 3/1997 | Delgado et al. |
| 5,785,960 A | 7/1998 | Rigg |
| 5,931,166 A | 8/1999 | Weber |

(Continued)

FOREIGN PATENT DOCUMENTS

EP    0226959    7/1987

(Continued)

*Primary Examiner* — Huyen Le
(74) *Attorney, Agent, or Firm* — S. Robert Chuey (57) ABSTRACT

An apparatus for modifying a keratinous surface that has a rotatable applicator that is in fluid communication with a first modification composition. The apparatus also has a sensor and a CPU. The sensor is positioned forward of the applicator head such that as the head rolls across the keratinous surface the sensor reads the portion of the keratinous surface in front of the rolling head. The sensor readings are transmitted to the CPU, the CPU analyzes the sensor readings of the keratinous surface, and the CPU sends a signal to the applicator head to treat or not to treat the analyzed surface. When the CPU sends a signal to the applicator to treat the surface, a small portion of the first modification composition is applied to the head such that when the head rolls over the keratinous surface the first modification composition contacts the area of the keratinous surface that needs treatment.

15 Claims, 4 Drawing Sheets

U.S. PATENT DOCUMENTS

| | | | |
|---|---|---|---|
| 5,931,595 A * | 8/1999 | Van Oost | 401/147 |
| 5,997,205 A * | 12/1999 | Koide | 401/147 |
| 6,035,860 A | 3/2000 | Mombourquette | |
| 6,035,867 A | 3/2000 | Barrick | |
| 6,067,996 A | 5/2000 | Weber | |
| 6,139,829 A | 10/2000 | Estrin | |
| 6,153,253 A | 11/2000 | Affeldt | |
| 6,190,730 B1 | 2/2001 | Matsos et al. | |
| 6,432,147 B1 | 8/2002 | Dias et al. | |
| 6,436,127 B1 | 8/2002 | Anderson et al. | |
| 6,461,467 B2 | 10/2002 | Blatchford et al. | |
| 6,502,583 B1 | 1/2003 | Utsugi | |
| 6,543,893 B2 | 4/2003 | Desormeaux | |
| 6,578,276 B2 | 6/2003 | Patton et al. | |
| 6,724,480 B2 | 4/2004 | De Rigal et al. | |
| 6,810,130 B1 | 10/2004 | Aubert et al. | |
| 7,066,962 B2 | 6/2006 | Swords | |
| 7,166,279 B2 | 1/2007 | Law | |
| 2002/0155069 A1 | 10/2002 | Pruche et al. | |
| 2003/0060810 A1 | 3/2003 | Syrowicz et al. | |
| 2004/0078278 A1 | 4/2004 | Dauga et al. | |
| 2004/0175347 A1 | 9/2004 | Bissett et al. | |
| 2006/0210513 A1 | 9/2006 | Luizzi et al. | |
| 2006/0275237 A1 | 12/2006 | Bissett et al. | |
| 2007/0035815 A1 | 2/2007 | Edgar et al. | |
| 2007/0049832 A1 | 3/2007 | Edgar et al. | |
| 2007/0148120 A1 | 6/2007 | Omura et al. | |
| 2007/0224158 A1 | 9/2007 | Cassin et al. | |

FOREIGN PATENT DOCUMENTS

| | | |
|---|---|---|
| EP | 0569291 | 11/1993 |
| EP | 0686512 | 12/1995 |
| FR | 2561515 | 9/1985 |
| GB | 2344776 | 6/2000 |
| JP | 1004189 | 1/1989 |
| JP | 9178560 | 7/1997 |
| JP | 11169231 | 6/1999 |
| JP | 2000194838 | 7/2000 |
| WO | WO9505892 | 3/1995 |
| WO | WO 98/52522 | 11/1998 |
| WO | WO9917668 | 4/1999 |
| WO | WO9933372 | 7/1999 |
| WO | WO 2008/098234 A2 | 8/2008 |
| WO | WO 2008/098235 A2 | 8/2008 |
| WO | WO 2008/100878 A1 | 8/2008 |
| WO | WO 2008/100880 A1 | 8/2008 |

* cited by examiner

APPARATUS AND METHODS FOR MODIFYING KERATINOUS SURFACES

CROSS REFERENCE TO RELATED APPLICATIONS

This application claims the benefit of U.S. Provisional Application No. 61/145,344, filed Jan. 16, 2009, U.S. Provisional Application No. 61/145,350, filed Jan. 16, 2009, U.S. Provisional Application No. 61/145,358, filed Jan. 16, 2009, U.S. Provisional Application No. 61/145,365, filed Jan. 16, 2009, U.S. Provisional Application No. 61/145,371, filed Jan. 16, 2009, and U.S. Provisional Application No. 61/145,378, filed Jan. 16, 2009.

FIELD OF THE INVENTION

This invention relates to an apparatus for applying compositions to skin, hair shafts and other keratinous surfaces. The compositions can modify color or structure of the keratinous surface. Structure modifications can include complete removal of hair from human skin and changing the texture of human skin.

BACKGROUND OF THE INVENTION

Make-up, hair colorants, hair growth compositions and hair removal compositions are known. But all of them share a common defect; they are exceedingly difficult to apply with precision. Make-up compositions are typically applied by macro methods. That is, a large area is covered with one composition, a cheek bone or eyelid, for example. Lip liners and eyeliners are relatively thick lines to accent or highlight the eyes and lips. But these methods are done manually, either to ones self or with help from another person. And again, they are large, highly visible accents of varying color. It is exceedingly difficult and extremely time consuming to apply minute amounts of make-up to ones face. And importantly, there has been no motivation to do such a limited application.

Hair removal compositions, commonly referred to as depilatories, are generally harsh chemicals. They are designed to be applied to unwanted hair. Depilatories remove the hair by essentially dissolving it. But existing technologies apply the depilatories to both the hair and the skin around the hair. This can result in irritation to the skin. Alternatively, formulators can make a depilatory that is not harsh to the skin, but this invariably makes the depilatory less effective.

Likewise, hair colorants are generally applied to the hair but necessarily they contact the skin around the hair. While hair colorants are often less offensive to the skin than are depilatories, they are harsh and can modify the color of the skin. Hair colorants are typically thick viscous compositions that are applied in bulk to hair in hopes that the composition will stick to the hair shafts and color the desired area. But it would be advantageous if a more precise method of application were available such that less viscous colorant can be used in smaller amounts to more precisely color only the desired area.

Finally, hair growth compositions are essentially poured onto the scalp in hopes that some will leach into the follicle pores were it is needed. Again, if a more precise method of application were available, small amounts of the hair growth composition could be directed to the pores where it is needed without drenching the entire scalp.

Therefore, there exists a need for methods and apparatuses that can precisely apply liquid compositions to small areas such as very fine facial hair, a portion of a hair shaft, or the pores of a hair follicle. These methods and apparatuses are defined by the present invention.

SUMMARY OF THE INVENTION

In one embodiment of the present invention there is provided an apparatus for modifying a keratinous surface that has a rotatable applicator that is in fluid communication with a first modification composition. The apparatus also has a sensor and a CPU. The sensor is positioned forward of the applicator head such that as the head rolls across the keratinous surface the sensor reads the portion of the keratinous surface in front of the rolling head. The sensor readings are transmitted to the CPU, the CPU analyzes the sensor readings of the keratinous surface, and the CPU sends a signal to the applicator head to treat or not to treat the analyzed surface. When the CPU sends a signal to the applicator to treat the surface, a small portion of the first modification composition is applied to the head such that when the head rolls over the keratinous surface the first modification composition contacts the area of the keratinous surface that needs treatment. The sensor readings made by the sensor contain a value for a characteristic selected from the group of color, brightness, reflectance, temperature, texture, and mixtures thereof. And the first modification composition is selected from the group consisting of inks, dyes, pigments, adhesives, curable compositions, optically activated compounds, hair colorants, hair removal compositions, hair growth stimulants, metal oxides, bleaching agents, texture reducing polymers, skin care compositions, and mixtures thereof.

In yet another embodiment of this invention there is provided a method for modifying a keratinous surface comprising the steps of: providing a sensor that reads the properties of a small portion of the keratinous surface; sending the readings to a CPU, which is programmed with a predetermined baseline value and at least one predetermined threshold value. The CPU compares the readings to the baseline value and calculates the variance between the reading and the baseline value. When that calculated variance exceeds the threshold the CPU sends a signal to an applicator which is activated to apply a portion of a first modification composition to the same portion of the keratinous surface that had the reading with a variance above the threshold value.

The present invention solves many problems with prior devices and methods. Specifically, with the apparatuses and methods of the present invention, the make-up, hair colorant, hair removal and hair growth compositions can be precisely applied where it is needed. This allows for the use of significantly less composition. Moreover, the surrounding keratinous surfaces that are not treated with the modification compositions are not irritated and are not unnecessarily colored. And when make-up is applied, the coverage on the skin is small but the result is a natural, and substantial improvement in the look of the consumer's skin.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

The present invention may be understood more readily by reference to the following detailed description of illustrative and preferred embodiments. It is to be understood that the scope of the claims is not limited to the specific compositions, methods, conditions, devices, or parameters described herein, and that the terminology used herein is not intended to be limiting of the claimed invention. Also, as used in the specification, including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent basis "about," it will be understood that the particular values form another embodiment. All ranges are inclusive and combinable.

All percentages and ratios used herein are by weight of the total composition, and all measurements made are at 25° C., unless otherwise designated.

The methods, apparatuses, and compositions of the present invention are best understood with reference to the method of use. Each of the process steps, the apparatuses and the compositions used in that step are described in turn below.

First, a potion of a keratinous surface, for example, hair or skin, is read with a sensor. The data from the sensor is analyzed by an analytical device, for example, a CPU. Based on the analysis, the portion of the keratinous analyzed surface is either treated or left untreated by an applicator. The applicator applies a modification composition if the analysis indicates that the surface needs to be treated.

The methods of reading the keratinous surface, the sensors used and the reading the keratinous surface and the analytical equipment are all described in the following published patent applications: WO 2008/098234 A2, Handheld Apparatus and Method for the Automated Application of Cosmetics and Other Surfaces, first filed 11 Feb. 2007; WO 2008/100878 A1, System and Method for Applying a Modification composition to Change a Person's Appearance Based on a Digital Image, first filed 12 Feb. 2007; WO 2008/098235 A2, System and Method for Providing Simulated Images Through Cosmetic Monitoring, first filed 11 Feb. 2007; WO 2008/100880 A1, System and Method for Applying Agent Electrostatically to Human Skin, first filed 12 Feb. 2007; US 2007/0049832 A1, System and Method for Medical Monitoring and Treatment Through Cosmetic Monitoring and Treatment, first filed 12 Aug. 2005; and US 2007/0035815 A1, System and Method for Applying a Modification composition to Improve the Visual Attractiveness of Human Skin, first filed 12 Aug. 2005; All six applications filed by Edgar et al. The entire disclosure of each of the six Edgar et al. applications is incorporated herein by reference.

Figure 1:
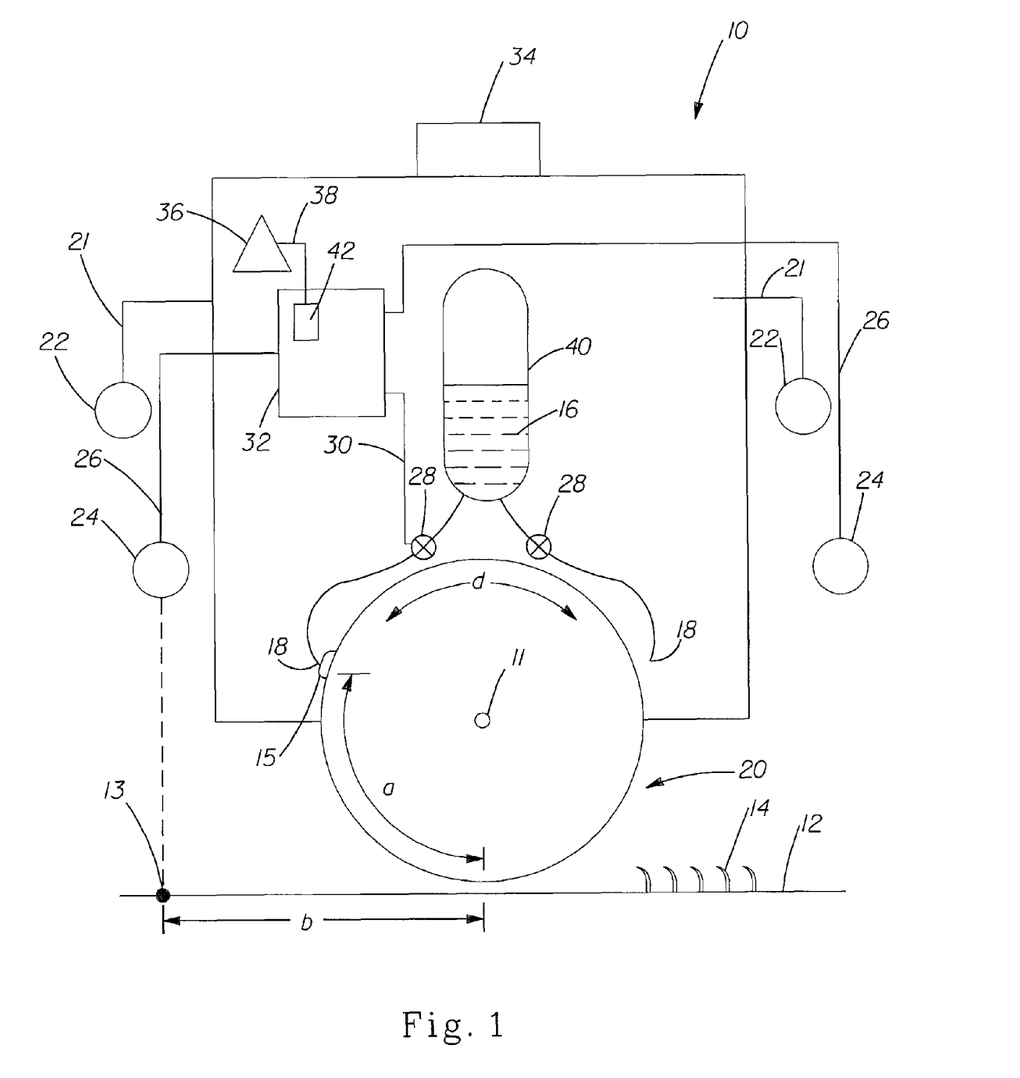
FIG. 1 is an apparatus according to the present invention.

The methods and apparatuses used by the present invention can be briefly summarized as follows. Referring now to FIG. 1, wherein apparatus 10 comprises applicator 20 and sensor 24, as described in the six Edgar et al. applications. Photo voltaic cells which read changes in voltage when the light hitting the cell is scattered, absorbed, or more highly reflected are just one example of sensors suitable for use in the present invention. Sensor 24 analyzes or "reads" a region of keratinous surface, for example, skin 12, hair 14 or both, and divides the reading into a plurality of frexels, and then measures at least one optical attribute of each of the plurality of frexels. From the optical attributes of the frexels, at least one measured characteristic affecting visual attractiveness is identified.

The term "frexel" is defined as a small pixel-like region of the keratinous surface. A frexel might correspond to a small portion of a freckle or other skin feature, or it may correspond to an area of the keratinous surface that does not have special features. The term frexel is used to suggest that what is being measured is on a 3-D surface rather than a flat surface. A region of keratinous surface is comprised of a plurality of frexels. For instance, if a resolution of 300 dots per inch (11.8 dots per mm or "dpmm") is used, a frexel may have a width and height of about 1/300th of an inch (0.085 mm) so that there are approximately 90,000 frexels per square inch (140 frexels per square mm). The surface of the human body may have millions of frexels.

Figure 2:
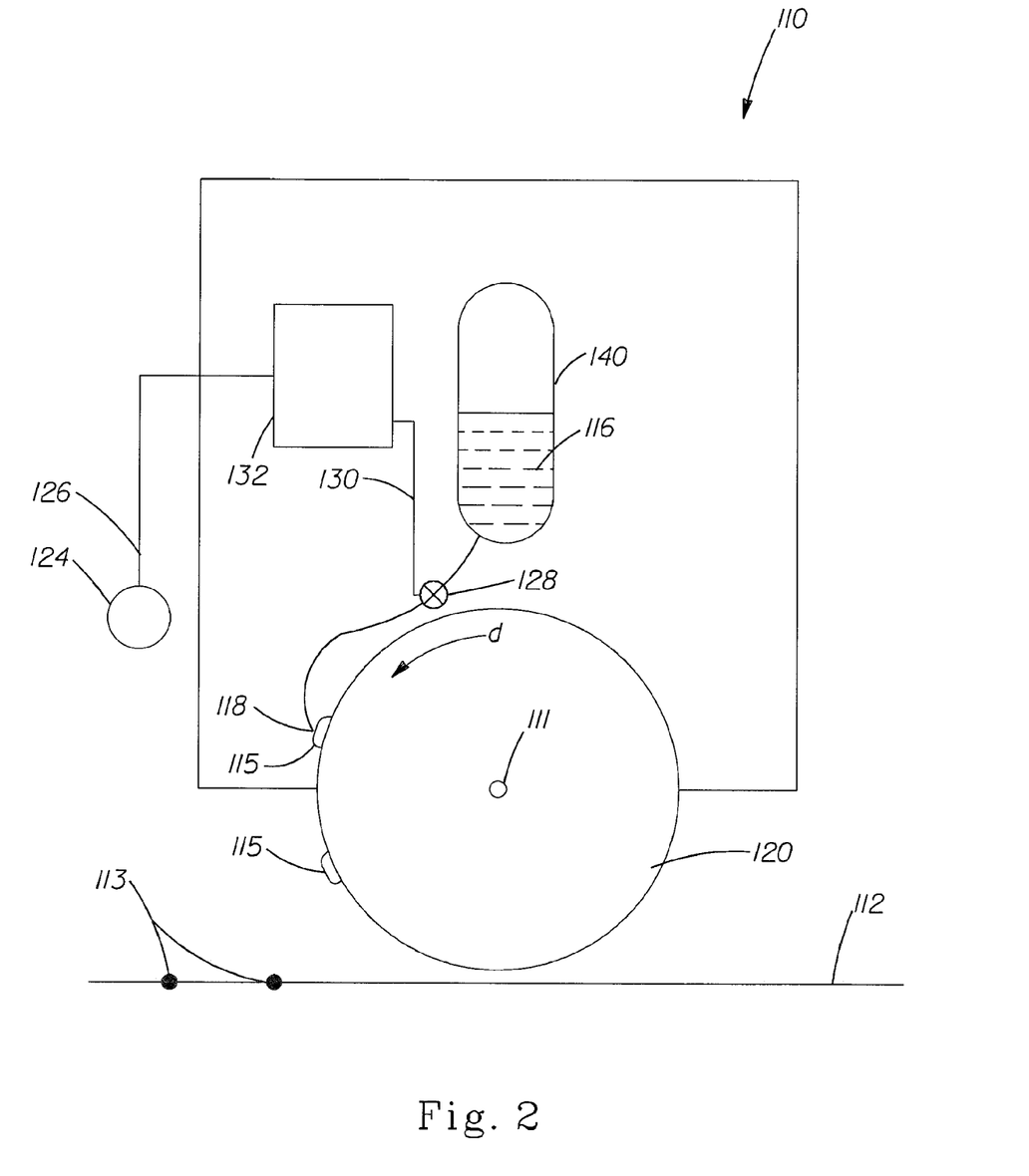
FIG. 2 is an apparatus according to the present invention before application of a modification composition.
Figure 3:
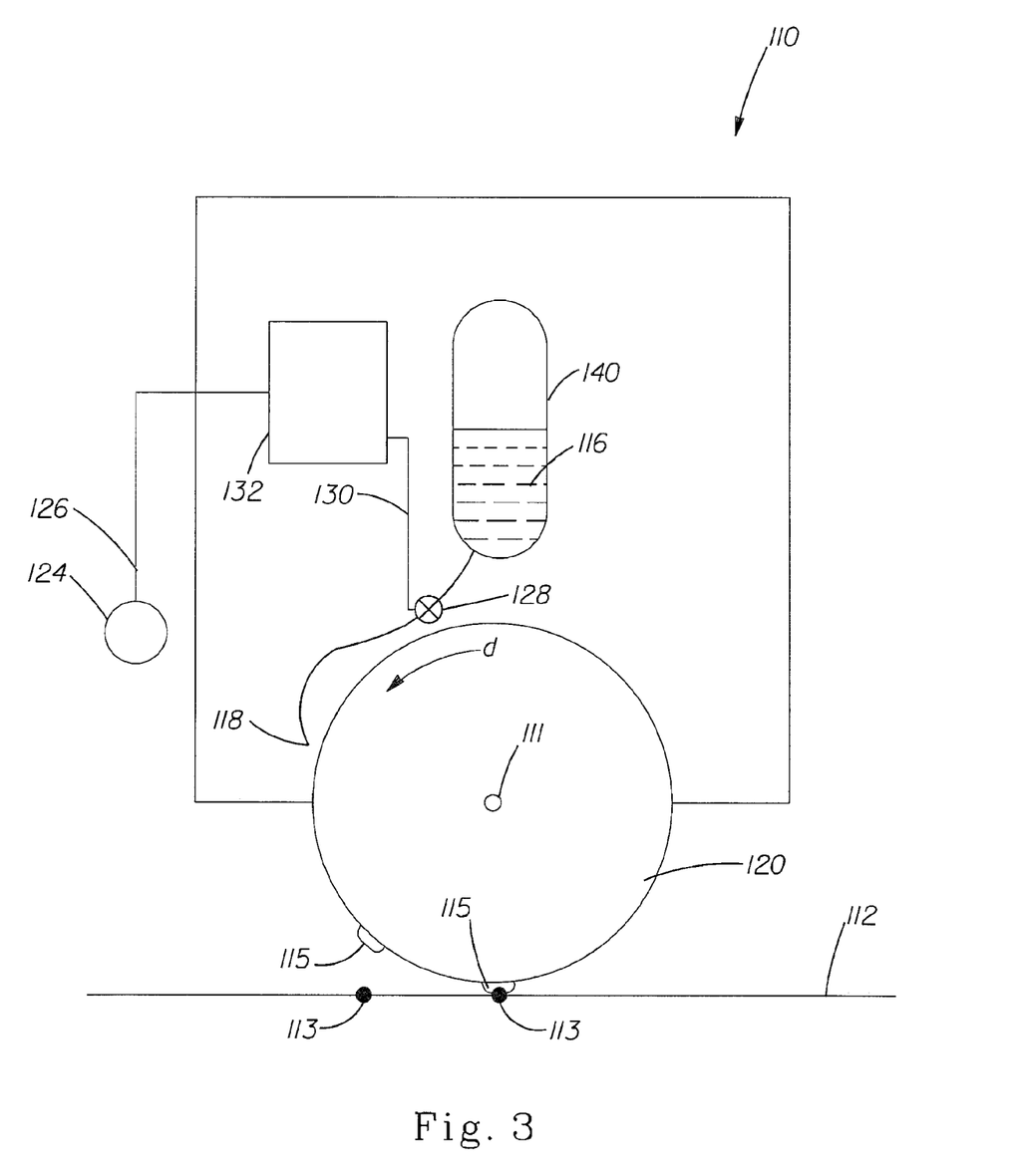
FIG. 3 is an apparatus according to the present invention during application of a modification composition.
Figure 4:
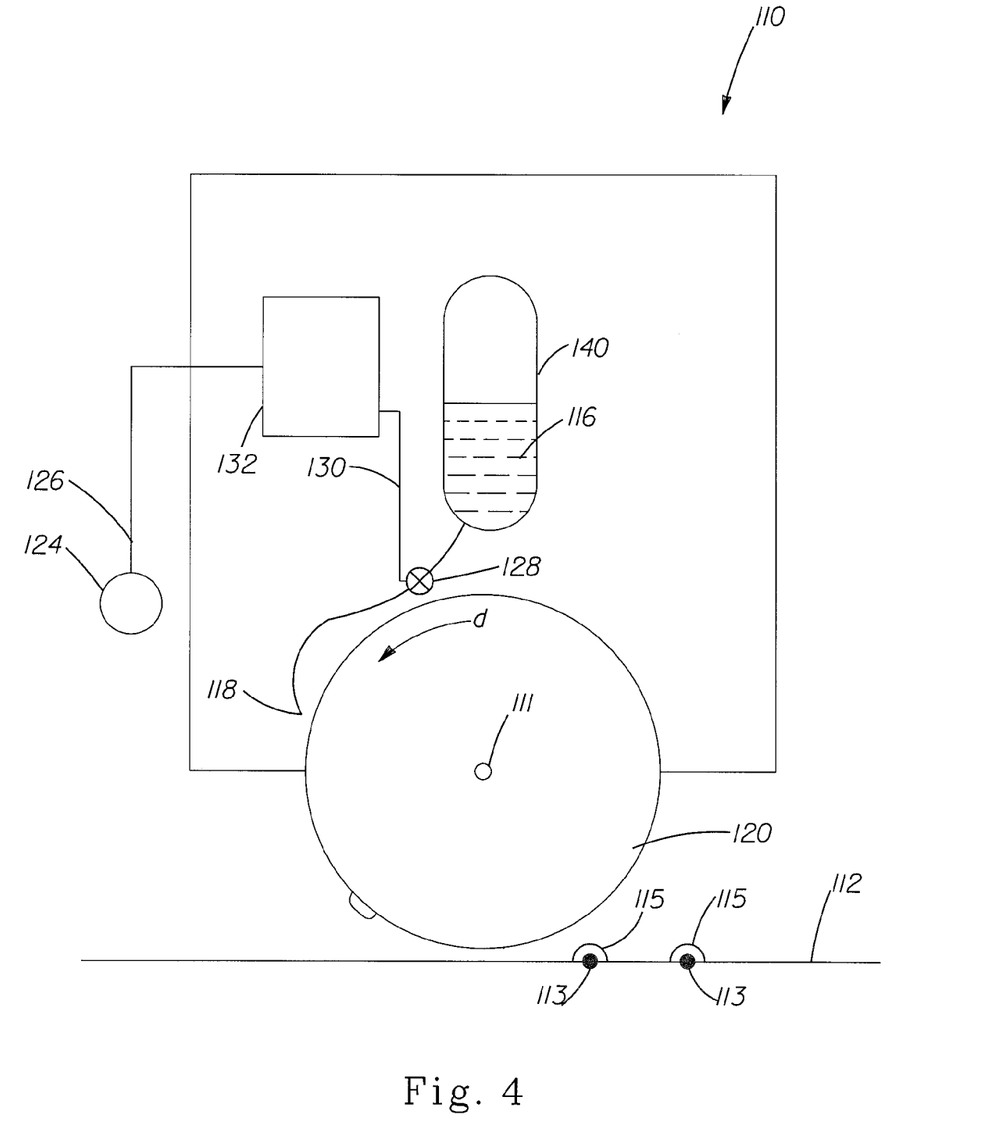
FIG. 4 is an apparatus according to the present invention after application of a modification composition.

Applicator 20 is a rotatable device that can be, for example, a disc, a cylinder, a ball or the like. Applicator 20 rotates about axis 11 in either direction "d". Although only one sensor is required, two are shown in FIG. 1. Each sensor 24 can be activated depending on which direction the applicator 20 is rolling. Sensor 24 is in electronic communication with CPU 32 via optional sensor lead 26. Wireless communication between any or all of the electronic elements is acceptable and may be preferred in certain embodiments. The reading from sensor 24 is transmitted to CPU 32 and a desired state of the keratinous surface characteristic is determined based on a predetermined look for the characteristic read. In the present invention optional valve 28 and opening 18 feed modification composition 16 to applicator 20 to form modification droplet 15. Applicator 20 continues to move across keratinous surfaces 12 and 14 (skin and hair, respectively). Optional valve 28 then dispenses at least one modification composition 16 through opening 18 to applicator 20 creating modification composition droplet 15. Applicator 20 continues to roll across keratinous surfaces 12 and 14 depositing modification composition droplet 15 on skin 12, hair 14 or both as shown in FIGS. 2-4 and described in greater detail below. It is preferred although not required that distance "a" be approximately equal to distance "b". Distance "a" is the distance from where modification composition droplet 15 is deposited on applicator 20 until it is rolled around until it contacts skin 12, hair 14 or both. Distance "b" is the distance from where sensor 24 reads treatment area 13 to the current contact position of applicator 20. Modification composition 16 is contained in reservoir 40 and can be dispensed through opening 18.

Other optional components include, but are not limited to, light source 22, light source lead 21, power source 42 and switch 34 to turn the apparatus on and off. In a preferred embodiment of the present inventions motion sensor 36 and optional motion sensor lead 38 is used to determine the speed that applicator 20 is moving across the keratinous surface, and what angle it is at in relation to the keratinous surface. All of these dimensions can be used to more accurately and more selectively deposit to modification composition 16.

Referring now to FIGS. 2, 3 and 4, which are simplified drawings of one apparatus 110. Apparatus 110 is shown in three stages of applying modification composition 116. Sensor 124 reads keratinous surface 112 and detects treatment area 113. A signal is sent from sensor 124 to CPU 132 via optional sensor lead 126. CPU 132 analyzes keratinous surface 112 based on a sensor reading. When a correction is desired, CPU 132 activates valve 128 via optional valve lead 130 to release a potion of modification composition 116 through opening 118 onto applicator 120 to form modification droplets 115. As shown in FIG. 2, applicator 120 continues to roll in direction "d" causing modification composition droplets 115 to move closer to treatment area 113. FIG. 3 shows applicator 120 rolling over treatment area 113 depositing modification droplets 115 onto them and FIG. 4 shows applicator rolling across keratinous surface 112 after application of modification composition droplets 115.

Optional valve 128 can be replaced by a simple wicking device, for example, a piece of porous material as used in commercially available felt tip markers. The tip can be moved into contact with applicator 120 when a modification droplet 115 is desired. Likewise, commercially available ball point pen technology can be used to dispense modification composition 116 onto applicator 120. Ink jet sprayers may be employed as well.

The programming of CPU 32 will be known to those skilled in the art. But the logic will include identifying a desired baseline or a desired optical property. Variations from the desired baseline can then be easily identified. After identification The CPU can instantly correct by applying the modification composition, or the operator can be notified of the variation and the operator trigger the correction if they so choose. For skin the baseline can be a particular color of skin or texture. For example, a freckle will be read as a localized dark color variation, and a wrinkle will be read as a textural abnormality. Again, modification compositions can be applied automatically, or selectively by the used depending on the control sequence for the device. The modification compositions used to lighten a freckle may be different than the agent used to fill in or smooth out a wrinkle. In the case of hair colorants, the baseline can be the desired color of hair. For hair removal applications, the baseline can be skin with no hair on it. In the case of hair growth agents, the baseline can be the pores from which hair grows. The threshold value can be a certain deviation from the baseline that requires correction. For hair color applications the threshold will be a change in color from the baseline indicating that the analyzed area of hair needs the hair colorant to be applied. Likewise, for hair removal, the texture of the skin can be measured and the change in texture will indicate the presence of an unwanted hair to which the hair removal composition is applied.

Finally, the apparatuses of this invention can be programmed to read skin 12 looking for pores that should contain hair shafts, contain unhealthy hair shafts, or contain hair shafts in an area of the scalp where hair loss is likely to occur (e.g. areas of male pattern baldness). The apparatus can apply a modification composition into the pore which can be, for example, a hair growth stimulant (such as the commercially available minoxidil). By this method, higher concentrations of the modification composition can be applied selectively to the exact area where it is needed.

Apparatus 10 is preferably handheld but can be tethered to a structure that moves the apparatus 10 across the keratinous surface to be modified. If handheld, the consumer would simply move apparatus 10 across the keratinous surface to be modified. Optionally, multiple apparatuses can be configured in a stationary structure wherein the consumer places the keratinous surface to be modified and multiple readings and applications occur simultaneously or in sequence.

In another embodiment, the modification composition can be applied to the keratinous surface by scanning and applying almost at the same time and making multiple passes over the surface. Several advantages result from using multiple pass application. The process for multiple pass applications is to make a partial application of the modification composition, then to scan again the area of skin that has received the partial application. A further application of modification compositions can be made, and still further multiple pass scanning and applications can be made to approach an aesthetic goal.

Modification compositions may be applied to applicator 20 with "flow control" devices or non-drop control devices. Flow control devices typically are characterized as "drop control techniques" where individual droplets of the substance are controlled. Ink jet printers, which are known to the art, are examples of drop on demand applicators and this technology is applicable for use n the present invention. Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, it is often desirable to provide very specific control of the amount and placement of the modification compositions.

Examples of drop control include "fine flow control" where the flow of the substance is precisely controlled to deliver droplets as desired; and "inkjet technologies." An older inkjet technology includes supplying a continuous flow of charged droplets past electrostatic deflector plates which are alternately charged so that the plates either permit a droplet to pass or deflect to a gutter. This technique was the original design basis for inkjet printers. Other inkjet technologies include "drop on demand" such as thermal devices provided by Hewlett Packard, and piezoelectric devices such as provided by Epson and other printer manufacturers. In one embodiment of the current invention, the drop on demand technology is combined with charging the droplets.

Those skilled in the art will appreciate that many skin defects occur below the surface. But these defects can be detected and treated. Accordingly, the keratinous surface has an outer surface of from about 1 mm to about 5 mm in thickness and an inner core directly below the outer surface, and wherein the sensor reads the inner core or the keratinous surface and then the applicator treats the outer surface to either mask or correct the inner defect.

It may be desirable for the apparatus to treat from about 1.0% to about 10% of the keratinous surface that is read by the sensor with a modification composition. In one embodiment of this invention the applicator applies from about 0.01 μg to about 100 μg of the first modification composition to the keratinous surface when the applicator is activated by the CPU. And the applicator may apply the first modification composition in droplets having an average diameter of from about from about 0.1 μm to about 50 μm.

Modification Compositions

The present invention may utilize a variety of modification compositions, for example, inks, dyes, pigments, adhesives, curable compositions, optically activated compounds, metal oxides (for example, TiO2), bleaching agents, texture reducing polymers, skin care compositions, hair colorants, hair removal compositions (often referred to as depilatories), hair growth stimulants and mixtures thereof.

The modification compositions of this invention can be delivered alone or in the presence of a dermatologically-acceptable carrier. The phrase "dermatologically-acceptable carrier", as used herein, means that the carrier is suitable for topical application to the keratinous tissue, has good aesthetic properties, is compatible with any additional components of the skin care composition, and will not cause any untoward safety or toxicity concerns. The carrier can be in a wide variety of forms. Non-limiting examples include simple solutions (water or oil based), emulsions, and solid forms (gels, sticks, flowable solids, amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions. The modification composition can be delivered in a variety of product forms including, but not limited to, a cream, a lotion, a gel, a foam, a paste, or a serum. Additionally, the modification composition can include for purposes of proper formulation and stabilization anti-fungal and anti-bacterial components.

Inks, dyes, metal oxides and pigments (collectively referred to as "colorants" below) are used to modify the color or reflectance of the keratinous surface. These compositions are commonly used to modify color and reflectance in cosmetic, "make-up" compositions. Foundation, lipstick, eyeliner are just a few examples of these compositions, but they are all applied evenly across large portions of the keratinous surface, that is they are macro-applications. In sharp contrast, the present modification compositions are selectively applied on a very small scale to select areas, that is, a micro application. Suitable colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Inorganic white or uncolored pigments include $TiO_2$, $ZnO$, or $ZrO_2$, which are commercially available from a number of sources. Other suitable colorants are identified in U.S. Pat. No. 7,166,279. Colorants are generally included at a weight percent such that the skin care composition yields a perceptible color. In one embodiment, the skin care composition exhibits a color that perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

Adhesives that are compatible with keratinous surfaces are known any such adhesive can be applied with the apparatuses of the present invention. Commercially available adhesives compatible with keratinous surfaces are available from the 3M Corporation of Minneapolis Minn. See, for example: U.S. Pat. No. 6,461,467, issued to Blatchford, et al., filed on Apr. 23, 2001; 5,614,310, issued to Delgado, et al., filed on Nov. 4, 1994; and 5,160,315, issued to Heinecke et al., filed on Apr. 5, 1991. The entire disclosures of these patent applications are incorporated by reference. After the adhesive is selectively applied to the keratinous surface, a second modification composition can be dusted on the keratinous surface where it will stick the adhesive. The second modification that is not adhered to the keratinous surface can then be removed leaving behind a selective, micro application of the second modification composition. Likewise compositions that cure upon exposure to certain wavelengths of energy, infrared light for example, are know to the art and can be applied by the apparatuses of the present invention. By this method, the curable composition is selectively applied to the keratinous surface and then it is cured by exposing the keratinous surface to the curing energy source. The entire keratinous surface can be exposed, or the exposure can be done at the same time as the application.

Wrinkle or texture reducing polymers and skin tightening are known. See, for example: U.S. Pat. No. 6,139,829, issued to Estrin on Oct. 31, 2000; and US Patent Applications US20060210513A1, filed by Luizzi, et al. on Mar. 21, 2005; US20070224158A1, filed by Cassin et al. on Mar. 18, 2005; and US20070148120A1, filed by Omura et al. on Jan. 14, 2005. The entire disclosures of this patent and these published patent applications are incorporated by reference. More specifically, a cosmetic process for softening the wrinkles of wrinkled skin may comprise applying, to the wrinkled skin, a cosmetic composition, in particular an anti-wrinkle composition, comprising, in a physiologically acceptable medium suitable for topical application to the skin of the face: from 0.1 to 20% by weight of at least one tensioning agent, with respect to the total weight of the composition.

Optically-activated particles can be used as or added to the modification compositions of this invention. Sometimes referred to a "interference pigments", these particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing light. These particles help to reduce the visual perception of skin imperfections, including cellulite, shadows, skin discolorations, and wrinkles. Each of the optically-activated particles are encapsulated with a UV transparent coating to increase the diffusion light to further reduce the visual perception of the skin imperfections. The encapsulated optically-activated particles are able to absorb ultraviolet radiation and emit visible light; and the encapsulated optically-activated particles are able to both scatter and absorb light in a diffuse manner in order to reduce the visual perception of skin imperfections, including cellulite, wrinkles, shadows, and skin discolorations, when the optically-activated particles are applied to the skin surface.

Hair colorants and hair removal compositions are also suitable for use with the apparatuses of the present invention. These compositions, and their component parts, are best described by the examples given below. Each of the individual chemical compositions described below for hair colorants can be used in combination with any of the others ingredients, and likewise, those skilled in the art will appreciate that the individual compositions given for depilatories can be used with other ingredients listed in other examples.

Skin care compositions can be applied with the apparatuses of this invention. The skin care composition may be used as, for example, a moisturizer, a conditioner, an anti-aging treatment, a skin lightening treatment, a sunscreen, a sunless tanner, and combinations thereof.

The skin care composition may comprise a safe and effective amount of one or more skin care active ("active") useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of a skin care active can be from about $1 \times 10^{-6}$ to about 25% by weight of the total composition, in another embodiment from about 0.0001 to about 25% by weight of the total composition, in another embodiment from about 0.01 to about 10% by weight of the total composition, in another embodiment from about 0.1 to about 5% by weight of the total composition, in another embodiment from about 0.2 to about 2% by weight of the total composition. Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, peptides, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. application publication No. US2006/0275237A1 and US2004/0175347A1.

The skin care composition may comprise a particulate material. Particles can range from mildly abrasive polymeric microbeads to moderately abrasive materials such as sodium bicarbonate to relatively aggressive materials such as alumina crystals. Particulate materials suitable for use herein include but are not limited to bismuth oxychloride, sericite, mica, mica treated with barium sulfate or other materials, zeolite, kaolin, silica, boron nitride, lauroyl lysine, nylon, polyethylene, talc, polypropylene, polystyrene, ethylene/acrylic acid copolymer, sericite, aluminum oxide, silicone resin, barium sulfate, calcium carbonate, cellulose acetate, PTFE, polymethyl methacrylate, starch, modified starches such as aluminum starch octenyl succinate, silk, glass, fibers, ground seeds, pumice, interference pigments, and mixtures thereof.

The skin care composition may also be a shaving gel or foam such as those described, for example, in U.S. Pat. No. 2,995,521 (Bluard), U.S. Pat. No. 3,541,581 (Monson), U.S. Pat. No. 4,405,489 (Sisbarro), U.S. Pat. No. 4,528,111 (Su), U.S. Pat. No. 4,651,503 (Anderson), U.S. Pat. No. 5,248,495 (Patterson), U.S. Pat. No. 5,308,643 (Osipow), U.S. Pat. No. 5,326,556 (Barnet), and U.S. Pat. No. 5,500,211 (George). Such compositions generally take the form of an oil-in-water emulsion in which the post-foaming agent, generally a volatile (i.e., low boiling point) aliphatic hydrocarbon, is solubilized in the oil phase, and the water phase comprises a water-dispersible soap, an interrupted soap component and/or a surfactant. The product is generally packaged in an aerosol container with a barrier, such as a piston or collapsible bag, to separate the post-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Hair Colorant Modification Compositions

Hair colouring compositions generally comprise an oxidising agent, and a developer. Optionally, a coupler may be used. Various aromatic compounds can be used as developers (also known as precursors or primary intermediates), together with various other compounds, commonly known as couplers. These are referred to as oxidative hair colouring agents because they require an oxidising agent for formation of colour. The compounds described as developers are those which react with oxidising agent to form a reactive oxidised intermediate. This intermediate then reacts with the coupler or couplers to give a coloured molecule. Some developers are capable of reacting with another molecule of the same type, i.e. self-coupling. Couplers do not generally react with oxidising agent but instead react with the reactive oxidised intermediate formed by reaction between the developer and the oxidising agent.

According to this invention hair colouring compositions comprise:

(i) at least one developer; and
(ii) at least one oxidising agent; and
(iii) optionally, at least one coupler.

Couplers, developers and oxidizing agents are generally described in WO98/52522 and U.S. Pat. Nos. 7,066,962, 6,432,147, the entire disclosure of these three references are incorporated herein by reference. Couplers can be used in amounts of from for instance 0.01 to 4%, preferably 0.01 to 2%, more preferably 0.03 to 3, eg 0.03 to 2%, and in some compositions not more than 1 or 0.5%. Total levels of developer and coupler generally vary according to the shade required. For blonde shades amounts of from 0.001 to 4 wt. % are preferred. For red shades amounts of 0.001 to 4 wt. % are preferred. For brown shades amounts of 0.01 to 4% are preferred. For black shades amounts of 0.1 to 4 wt. % are preferred.

A preferred oxidising agent is hydrogen peroxide. This is often used in amounts up to 10 wt. %, based on weight of composition applied to the hair. Other oxidising agents which may be used include other inorganic peroxygen oxidising agents, preformed organic peroxyacid oxidising agents and other organic peroxides such as urea peroxide, melamine peroxide, and mixtures of any of these.

Suitable oxidising agents are preferably water-soluble, that is they have a solubility of at least about 5 g in 1,000 ml of deionised water at 25° C. ('Chemistry' C. E. Mortimer, 5th Edition, page 277).

Usually the colouring compositions of the invention have pH above 7, in particular above pH 8 or 9. A pH of from 9 to 12 is often suitable. The systems of the invention can also be incorporated into low pH (eg pH 1 to 6) hair colouring systems.

Example 1

The following composition shown in Table 1 can be used for dyeing Piedmont hair. 100 g of the dyeing composition is mixed with 100 g of 20 volume hydrogen peroxide. The resulting mixture is applied to the hair and permitted to remain in contact with the hair for 30 minutes. The dyed hair is then shampooed, rinsed with water and dried. The ranges of ingredients set out in Table 1 are illustrative of useful concentrations of the recited materials in a hair dye product.

TABLE 1

Composition for Dyeing Hair

| Ingredients | Range (wt %) | Weight (%) |
|---|---|---|
| Cocamidopropyl betaine | 0-25 | 17.00 |
| Polyquaternium-22 | 0-7 | 5.00 |
| Monoethanolamine[1] | 0-15 | 2.00 |
| Oleic Acid | 2-22 | 0.75 |
| Citric Acid | 0-3 | 0.10 |
| 28% Ammonium hydroxide[1] | 0-15 | 5.00 |
| Behentrimonium chloride | 1-5 | 0.50 |
| Sodium sulfite | 0-1 | 0.10 |
| EDTA | 0-1 | 0.10 |
| Erythorbic acid | 0-1 | 0.40 |
| Ethoxydiglycol | 1-10 | 3.50 |
| C11-15 Pareth-9 (Tergitol 15-S-9) | 0.5-5 | 1.00 |
| C12-15 Pareth-3 (Neodol 25-3) | 0.25-5 | 0.50 |
| Isopropanol | 2-10 | 4.00 |
| Propylene glycol | 1-12 | 2.00 |
| p-Phenylenediamine[2] | 0-5 | 2 mmoles |
| N,N-Bis(hydroxyethyl)-p-phenylene diamine[2] | 0-5 | 2 mmoles |
| 3-Methyl-p-aminophenol[2] | 0-5 | 1 mmoles |
| p-Aminophenol[2] | 0-5 | 2 mmoles |
| Coupler* | 0.5-5 | 4 mmoles |
| 5-Amino-2-Methyl Phenol | 0-5 | 1 mmoles |
| 2,4-Diaminophenoxyethanol | 0-5 | 1 mmoles |
| m-Phenylenediamine | 0-5 | 1 mmoles |
| Water | qs to 100.00 | qs to 100.00 |

[1]In the aggregate, these ingredients are in the range of 2 to 15% by weight.
[2]At least one of these dye precursors is typically present.
*Couplers were chosen depending on the desired hair color from the group consisting of: 3-(N-acetyl) amino-1-phenol-2-pyrazolin-5-one (NAPP); 2,6-dichloro-para-aminophenol (DCP); paraphenylene diamine (PPD); 1.2% 3-acetamido phenol (3AP); and mixtures thereof.

Hair Removal Compositions

Numerous hair removal compositions are exemplified below. Typically these compositions contain two general components: a carrier and an active. Common carriers can be selected from the group consisting of water, alcohols, glycols, glycerin and mixturese thereof. The actives are best described by the various examples given below.

Example 2

A topical composition is prepared by combining the following components utilizing conventional mixing techniques and the pH is adjusted to 6.0 by adding NaOH.

| Component | % by wt. |
|---|---|
| N-acetyl-L-cysteine (Active) | 5.0 |
| Propylene glycol | 45.0 |
| Ethanol | 30.0 |
| Water | 20.0 |

1000.mg of the composition per 100 cm$^2$ skin is topically applied to the face twice per day to remove unwanted vellus hair.

Example 3

A topical composition is prepared by combining the following components utilizing conventional mixing techniques and the pH is adjusted to 4.5 by adding NaOH.

| Component | % by weight |
|---|---|
| Thioglycolic acid (Active) | 2.0 |
| Propylene glycol | 57.0 |
| Ethanol | 20.0 |
| Water | 10.0 |
| Benzyl alcohol | 4.0 |
| Glycerin | 5.0 |
| Myristyl alcohol | 2.0 |

4000.mg of the composition per 100 cm$^2$ skin is topically applied once a day to the legs to soften terminal hair.

Example 4

A topical composition is prepared by combining the following components utilizing conventional mixing techniques and the pH is adjusted to about 3.0 by adding NaOH.

| Component | % by weight |
|---|---|
| Glutathione (Active) | 1.0 |
| Propylene glycol | 30.0 |
| Glycerin | 3.0 |
| Water | 66.0 |

2000.mg of the composition per 100 cm$^2$ skin is topically applied twice per day to the face to remove unwanted vellus hair.

Example 5

A topical composition is prepared by combining the following components utilizing conventional mixing techniques and the pH is adjusted to 5.0 by adding NaOH.

| Component | % by weight |
|---|---|
| N-acetyl-L-cysteine (Active) | 0.5 |
| Propylene glycol | 30.0 |
| Propylene glycol laurate | 1.0 |
| Isopropanol | 20.0 |
| Water | 48.5 |

500.mg of the composition per 100 cm$^2$ skin is topically applied once per day to the face to remove unwanted vellus hair.

Example 6

A lotion is prepared by combining the following components utilizing conventional mixing techniques and the pH is adjusted to 4.0 by adding NaOH.

| Component | % by weight |
| --- | --- |
| Cysteine (Active) | 5.0 |
| Di-partially hydrogenated tallow | 4.0 |
| Cetyltrimethyl ammonium chloride | 2.0 |
| DC-200 fluid (12500 csk)* | 1.0 |
| Citric acid | 3.5 |
| Ethylene glycol distearate | 1.5 |
| PEG-3 $C_{12}$ alkyl amide | 3.0 |
| Water | 80.0 |

*Dimethylpolysiloxane available from by Dow Chemical Co.

100.mg of the composition per 100 $cm^2$ skin is topically applied to the face three times a day to remove unwanted vellus hair.

Example 7

A water-in-oil emulsion is prepared by combining the following ingredients, using conventional mixing techniques and the pH is adjusted to 6.5 by adding NaOH.

| Component | % by weight |
| --- | --- |
| Oily Phase | |
| Lipoic acid (Active) | 5.0 |
| Cetearyl alcohol | 5.0 |
| Silicon oil, 200 fluid | 1.0 |
| Isopropyl myristate | 2.0 |
| Sodium stearoyl-2-lactylate | 2.0 |
| Aqueous Phase | |
| Propylene glycol | 5.0 |
| Sodium citrate | 0.2 |
| Perfume | 0.1 |
| Water | 79.7 |

The emulsion is prepared by taking 10 parts of the oily phase and adding it slowly with stirring to 90 parts by volume of the aqueous phase. Use of an amount of the emulsion to deposit about 1000 mg per 100 $cm^2$ of the emulsion three times a day to the legs is appropriate, after initial hair is removed by shaving. Replacement terminal hair is softer than the hair removed.

Example 8

An oil-in-water cream is prepared by mixing the following components and the pH is adjusted to 3.5 by adding NaOH.

| Component | % by weight |
| --- | --- |
| Oily Phase | |
| N-acetyl-L-cysteine (Active) | 5.0 |
| Sorbitan monoleate | 20.0 |
| Quaternium-18-hectonite | 5.0 |
| Liquid paraffin | 60.0 |

| Component | % by weight |
| --- | --- |
| Aqueous Phase | |
| Xanthan gum 1.0 | 1.0 |
| Preservative | 0.3 |
| Perfume | 0.2 |
| Water | 8.5 |

The cream is prepared by mixing the oily phase and heating to 65° C. The aqueous phase is combined and heated to 70° C. The aqueous phase is added to the oil phase with suitable agitation. Moderate agitation is applied while cooling. About 5 mg of the cream is deposited per 100 $cm^2$ on the face once a day to remove unwanted vellus hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for modifying a keratinous surface comprising:
    a rotatable applicator which is in fluid communication with
        a first modification composition;
    a sensor;
    a CPU;
    wherein the sensor is positioned forward of the applicator such that as the applicator rolls across the keratinous surface the sensor reads the portion of the keratinous surface in front of the rolling applicator, the readings are transmitted to the CPU, the CPU analyzes the sensor readings of the keratinous surface, the CPU sends a signal to the applicator head to treat or not to treat the analyzed surface, and wherein when the CPU sends a signal to the applicator to treat the surface, a small portion of the first modification composition is applied to the applicator such that when the applicator rolls over the keratinous surface the first modification composition contacts the area of the keratinous surface that needs treatment.

2. The apparatus of claim 1, where the apparatus has an applicator opening that is in fluid communication with a reservoir containing the first modification composition.

3. The apparatus of claim 2, wherein the applicator opening further comprises a wick that deposits the first modification composition onto the applicator when the wick contacts the applicator.

4. The apparatus of claim 2, where the applicator opening further comprises a printer head that sprays the first modification composition onto the applicator.

5. The apparatus according to claim 1, wherein the first modification composition is an adhesive, and after the apparatus treats the keratinous surface, a second modification composition is applied to the keratinous surface which sticks to the adhesive completing the modification of the keratinous surface.

6. The apparatus according to claim 1, wherein from about 1.0% to about 10% of the keratinous surface that is read by the sensor is modified by application of the first modification composition.

7. The apparatus according to claim 1, wherein the applicator applies from about 0.01 μg to about 100 μg of the first modification composition to the keratinous surface when the applicator is activated by the CPU.

8. The apparatus according to claim 1, further comprising a second modification composition.

9. The apparatus according to claim 1, wherein the readings made by the sensor contain a value for a characteristic selected from the group of color, brightness, reflectance, temperature, texture, and mixtures thereof.

10. The apparatus according to claim 1, wherein the first modification composition is selected from the group consisting of inks, dyes, pigments, adhesives, curable compositions, optically activated compounds, hair colorants, hair removal compositions, hair growth stimulants, metal oxides, bleaching agents, texture reducing polymers, skin care compositions, and mixtures thereof.

11. The apparatus according to claim 1, wherein the keratinous surface has an outer surface of from about 1 mm to about 5 mm in thickness and an inner core directly below the outer surface, and wherein the sensor reads the inner core or the keratinous surface.

12. The apparatus according to claim 1, wherein the applicator applies the first modification composition in droplets having an average diameter of from about from about 0.1 μm to about 50 μm.

13. An apparatus for modifying a keratinous surface comprising:
   a rotatable applicator which is in fluid communication with a first modification composition;
   a sensor;
   a CPU;
wherein the sensor is positioned forward of the applicator such that as the applicator rolls across the keratinous surface the sensor reads the portion of the keratinous surface in front of the rolling applicator, the readings are transmitted to the CPU, the CPU analyzes the sensor readings of the keratinous surface, the CPU sends a signal to the an operator of the device, the operator then chooses to treat or not to treat the identified portion of the keratinous surface, when the operator chooses to treat the portion of the keratinous surface she activates the CPU to apply a small portion of the first modification composition to the applicator such that when the applicator rolls over the keratinous surface the first modification composition contacts the area of the keratinous surface that needs treatment.

14. The apparatus according to claim 13, wherein the signal sent to the operator is selected from the group consisting of visual, auditory, tactile and mixtures thereof.

15. An apparatus for modifying a keratinous surface comprising:
   A rotatable applicator which is in fluid communication with a first modification composition;
   a sensor;
wherein the sensor is positioned forward of the applicator such that as the applicator rolls across the keratinous surface the sensor reads the portion of the keratinous surface in front of the rolling applicator, the readings are compared to a pre-determined baseline, any variation from the baseline is compared to a pre-determined threshold, if the threshold is exceeded the sensor sends a signal to the applicator to treat the analyzed surface, then a small portion of the first modification composition is applied to the applicator such that when the applicator rolls over the keratinous surface the first modification composition contacts the area of the keratinous surface that needs treatment.

* * * * *